United States Patent
Várkuti et al.

(10) Patent No.: US 12,214,202 B2
(45) Date of Patent: Feb. 4, 2025

(54) ON-LINE AUTOCALIBRATION METHOD FOR A COMPUTER BRAIN INTERFACE DEVICE AND COMPUTER BRAIN INTERFACE DEVICE

(71) Applicant: CEREGATE GMBH, Munich (DE)

(72) Inventors: Bálint Várkuti, Munich (DE); Saman Hagh-Gooie, Hamburg (DE); Brian Blischak, San Diego, CA (US)

(73) Assignee: Ceregate GmbH, Munich (DE)

( * ) Notice: Subject to any disclaimer, the term of this patent is extended or adjusted under 35 U.S.C. 154(b) by 690 days.

(21) Appl. No.: 17/224,953

(22) Filed: Apr. 7, 2021

(65) Prior Publication Data
US 2022/0323763 A1    Oct. 13, 2022

(51) Int. Cl.
*A61N 1/36* (2006.01)
*G06F 3/01* (2006.01)

(52) U.S. Cl.
CPC ..... *A61N 1/36139* (2013.01); *A61N 1/36132* (2013.01); *A61N 1/36171* (2013.01);
(Continued)

(58) Field of Classification Search
CPC ................ A61N 1/0534; A61N 1/0551; A61N 1/36057; A61N 1/36062; A61N 1/36082;
(Continued)

(56) References Cited

U.S. PATENT DOCUMENTS

| | | |
|---|---|---|
| 4,445,512 A | 5/1984 | Krupka et al. |
| 4,488,555 A | 12/1984 | Imran |

(Continued)

FOREIGN PATENT DOCUMENTS

| | | |
|---|---|---|
| DE | 102019202666 A1 | 8/2020 |
| DE | 102019209096 A1 | 12/2020 |

(Continued)

OTHER PUBLICATIONS

European Search Report issued in European Application No. 22151438.3, mailed on Jun. 17, 2022, 4 pages.

(Continued)

*Primary Examiner* — Amanda K Hulbert
(74) *Attorney, Agent, or Firm* — Kowert, Hood, Munyon, Rankin & Goetzel, P.C.; Jeffrey C. Hood; Luke S. Langsjoen

(57) ABSTRACT

A computer brain interface (CBI) device of an individual is self-calibrated. A neurostimulation test signal is generated based on a selected set of test signal parameters. The neurostimulation signal is applied to the afferent sensory nerve fibers to elicit a bioelectric response via a neurostimulation interface operably connected to or integrated with the CBI device. The neurostimulation interface senses the bioelectric responses of the stimulated afferent sensory nerve fibers. The CBI devices determines, based on the sensed bioelectric responses, whether an excitation behavior of the stimulated afferent sensory nerve fibers with respect to the neurostimulation interface has changed. When the excitation behavior has changed, a set of recalibrated neurostimulation signal parameters is determined based on the sensed bioelectric responses. The CBI device is operated using the recalibrated neurostimulation signal parameters to communicate information to the individual via neurostimulation of the afferent sensory nerve fibers.

20 Claims, 6 Drawing Sheets

Figure 1:
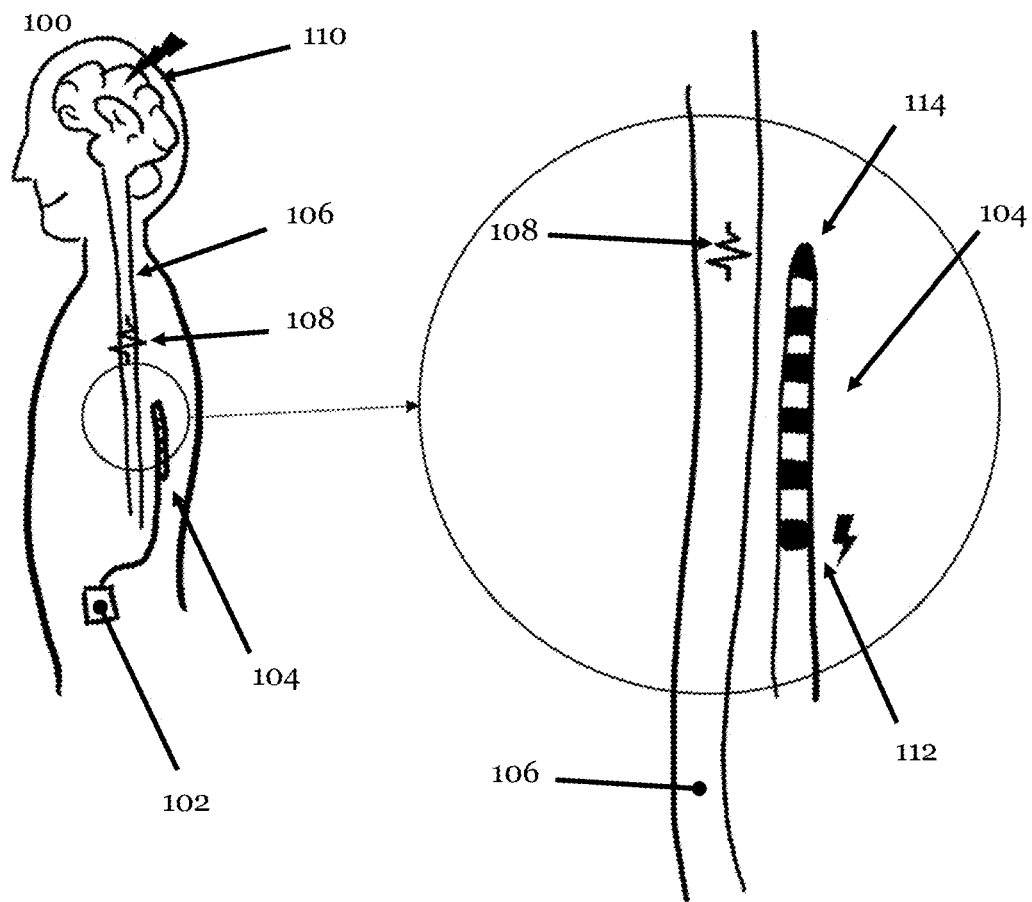

(52) U.S. Cl.
CPC ..... *A61N 1/36175* (2013.01); *A61N 1/36178* (2013.01); *G06F 3/015* (2013.01)

(58) Field of Classification Search
CPC .............. A61N 1/36139; A61N 1/3615; A61N 1/36167; A61N 1/36171; A61N 1/36178; A61N 1/37247; A61N 1/36003; A61N 1/36132; A61N 1/36175; A61N 1/37241; A61N 1/3606; A61N 1/36135; A61N 1/36185; G06F 3/015
See application file for complete search history.

(56) References Cited

U.S. PATENT DOCUMENTS

| | | | |
|---|---|---|---|
| 7,751,884 | B2 | 7/2010 | Ternes et al. |
| 7,774,056 | B2 | 8/2010 | Torgerson |
| 8,193,766 | B2 | 6/2012 | Rondoni et al. |
| 8,290,596 | B2 | 10/2012 | Wei et al. |
| 8,352,029 | B2 | 1/2013 | Ternes et al. |
| 8,364,271 | B2 | 1/2013 | De Ridder |
| 8,380,314 | B2 | 2/2013 | Panken et al. |
| 8,423,145 | B2 | 4/2013 | Pless et al. |
| 8,475,172 | B2 | 7/2013 | Lieberman et al. |
| 8,494,633 | B2 | 7/2013 | Tobacman |
| 8,509,904 | B2 | 8/2013 | Rickert et al. |
| 8,812,128 | B2 | 8/2014 | Kothandaraman |
| 9,095,314 | B2 | 8/2015 | Osorio et al. |
| 9,357,938 | B2 | 6/2016 | Ang et al. |
| 9,636,497 | B2 | 5/2017 | Bradley et al. |
| 9,713,720 | B2 | 7/2017 | Zhu |
| 9,974,478 | B1 | 5/2018 | Brokaw et al. |
| 10,568,559 | B2 | 2/2020 | Parker et al. |
| 2003/0065366 | A1 | 4/2003 | Merritt et al. |
| 2006/0129205 | A1 | 6/2006 | Boveja et al. |
| 2006/0241717 | A1 | 10/2006 | Whitehurst et al. |
| 2006/0241718 | A1 | 10/2006 | Tyler et al. |
| 2007/0027397 | A1 | 2/2007 | Fischell et al. |
| 2007/0250134 | A1 | 10/2007 | Miesel et al. |
| 2008/0129517 | A1 | 6/2008 | Crosby et al. |
| 2008/0139954 | A1 | 6/2008 | Day et al. |
| 2009/0306741 | A1 | 12/2009 | Hogle et al. |
| 2010/0057161 | A1 | 3/2010 | Machado et al. |
| 2010/0063411 | A1 | 3/2010 | Donoghue et al. |
| 2013/0150914 | A1 | 6/2013 | Kelly et al. |
| 2013/0253299 | A1 | 9/2013 | Weber et al. |
| 2014/0081348 | A1 | 3/2014 | Fischell |
| 2014/0379046 | A1 | 12/2014 | Tcheng et al. |
| 2015/0018724 | A1 | 1/2015 | Hsu et al. |
| 2015/0073492 | A1 | 3/2015 | Kilgard et al. |
| 2015/0290453 | A1 | 10/2015 | Tyler et al. |
| 2016/0022992 | A1 | 1/2016 | Franke et al. |
| 2016/0121118 | A1 | 5/2016 | Franke et al. |
| 2017/0080226 | A1 | 3/2017 | Akhoun |
| 2018/0050198 | A1 | 2/2018 | Mazanec et al. |
| 2018/0229046 | A1 | 8/2018 | Parker et al. |
| 2019/0030338 | A1 | 1/2019 | Wu et al. |
| 2020/0269049 | A1 | 8/2020 | Varkuti |
| 2020/0376272 | A1 | 12/2020 | Block et al. |

FOREIGN PATENT DOCUMENTS

| | | | |
|---|---|---|---|
| EP | 2552304 | B1 | 9/2015 |
| EP | 3229893 | A1 | 10/2017 |
| EP | 3431138 | A1 | 1/2019 |
| EP | 2486897 | B1 | 5/2019 |
| KR | 20170132055 | | 12/2017 |
| KR | 101841625 | B1 | 5/2018 |
| WO | 2012003451 | A3 | 1/2012 |
| WO | 2016116397 | A1 | 7/2016 |
| WO | 2018057667 | A1 | 3/2018 |
| WO | 2018109715 | A1 | 6/2018 |
| WO | 2020174051 | A1 | 9/2020 |

OTHER PUBLICATIONS

International Search report and Written Opinion in International Application No. PCT/EP2022/059282, mailed on Jul. 11, 2022, 21 pages.
Donati, A., Shokur, S., Morya, E. et al. "Long-Term Training with a Brain-Machine Interface-Based Gait Protocol Induces Partial Neurological Recovery in Paraplegic Patients" Sci Rep 6, 30383 (2016); https://doi.org/10.1038/srep30383, 16 pgs.
Examination Report for German Application No. 1020192014752.6, dated Jun. 16, 2020, 8 pgs.
First Office Action issued Oct. 16, 2019 for German Application No. DE 10 2019 202 666.4, 14 pp.
Heming EA et al: Designing a Thalamic Somatosensory Neural Prosthesis: Consistency and Persistence of Percepts Ecoked by 1 Electrical Simulation, IEEE Transactions on neural Systems and Rehabilitatinonengineering; IEEE Service Center, New York, vol. 19, No. 5, 6 pgs.
Invitation to Pay Additional Fees and, Where Applicable, Protest Fee and Partial International Search Report for PCT/EP2020/055156, date mailed May 29, 2020, 21 pgs.
Beauchamp et al., "Dynamic Electrical Stimulation of Sites in Visual Cortex Produces Form Vision in Sighted and Blind Humans," bioRxiv preprint, http://dx.doi.org/10.1101/462697, Nov. 5, 2018.
Lee et al., "Engineering Artificial Somatosensation Through Cortical Stimulation in Humans," Frontiers in Systems Neuroscience, www.frontiersin.org, Jun. 4, 2018, vol. 12, Article 24.
Roelfsema et al., "Mind Reading and Writing: The Future of Neurotechnology," Trends in Cognitive Sciences, https://doi.org/10.1016/j.tics.2018.04.001, May 6, 2018, Elsevier Ltd.
Anderson et al., "Optimized Programming Algorithm for Cylindrical and Directional Deep Brain Stimulation Electrodes," https://doi.org/10.1088/1741-2552/aaa14b, Journal of Neural Engineering, Jan. 24, 2018, IOP Publishing Ltd.
Swan et al., "Sensory Percepts Induced by Microwire Array and DBS Microstimulation in Human Sensory Thalamus," https://doi.org/10.1016/j.brs.2017 .10.017, Brain Stimulation 11 (2018) 416-422, Elsevier Inc.
Yadav, A.P., Li, D. & Nicolelis, M.A.L. : "A Brain to Spine Interface for Transferring Artificial Sensory Information". Sci Rep 10, 900 (2020), 15 pgs.
"Sensory Electrical Stimulation Cueing May Reduce Freezingof Gait Episodes in Parkinson's Disease"; L. Rosenthal et. al.; Hindawi Journal of Healthcare Engineering; 2018, Article ID 4684925, 6 pgs.
"Effect of rhythmic auditory cueingon parkinsonian gait: A systematic review and meta-analysis"; S. Ghai et al.; Nature Scientic Reports; (2018) 8:506; DOI:10.1038/s41598-017-16232-5, 19 pgs.
Examination Report for German Application No. 1020192014752.6, dated Apr. 16, 2021, 5 pgs.
European Search Report for European Application No. 21168408.9, mailed on Oct. 6, 2021, 4 pages.

ON-LINE AUTOCALIBRATION METHOD FOR A COMPUTER BRAIN INTERFACE DEVICE AND COMPUTER BRAIN INTERFACE DEVICE

1. TECHNICAL FIELD

The present invention relates to a closed-loop autocalibration method for a computer brain interface (CBI) device that may be carried out repeatedly and in an on-line manner while the CBI device is used for communicating general information to a person using the CBI device.

2. TECHNICAL BACKGROUND

Several promising approaches for implementing a general-purpose CBI are based on implantable neurostimulation systems that typically include one or more neurostimulation electrodes implanted at a desired stimulation site within or close to the nervous system of a person. A neurostimulator (e.g., an implantable pulse generator (IPG)) typically generates neurostimulation signals that are then applied to the neurostimulation electrodes in order to elicit a neural response (e.g. action potentials) in specific parts of the nervous system. For instance, DE 10 2019/202666, US 2020/0269049 and WO 2020/174051 describe such general-purpose CBI devices and systems that use direct neurostimulation of afferent sensory pathways to communicate abstract conceptual information directly to the brain of an individual.

For such CBI devices and systems to work reliably even in normally behaving (e.g. moving) individuals it has to be ensured that a given neurostimulation signal (or sequence of neurostimulation signals) that for instance is associated with a given piece/block of abstract information to be communicated consistently evokes essentially the same neural response in the brain or nervous system of the individual (e.g. a touch sensation in the left hand associated with a movement instruction or balance support cue etc.).

In this context, due to positional sensitivity a problem occurs, when neurostimulation electrodes that have initially been calibrated to elicit a certain neural response when being provided with a specific neurostimulation signal move relative to the stimulation target (e.g. afferent sensory axons/nerve fibers terminating in a desired sensory cortex area of the individual). For instance, such a situation may occur when during a movement (e.g. a person changing its body posture from standing to sitting or lying, a person bending over, coughing, etc.) the distance between a spinal cord stimulation electrode and the target nerve fibers in the spinal cord changes. As a result, the same neurostimulation signal that has previously been calibrated for a specific relative orientation and/or distance between electrode and spinal cord nerve fiber will not elicit the same desired neural response. In the prior art this distance is sometimes called dCSF, The present invention provides an autocalibration method for such CBI devices and systems that may run autonomously in an on-line manner and that may not necessitate intervention by trained medical personnel.

In this technical context, EP 3 229 893 B1 discloses a method of communicating along a neural pathway, comprising stimulating the neural pathway at a first location by delivering a peripheral sensory input, in order to evoke neural responses which propagate along the neural pathway, the neural responses being modulated with data, an implanted device sensing the evoked neural responses at a second location spaced apart from the first location along the neural pathway, and the implanted device demodulating the sensed neural responses to retrieve the data, the data being configured to control or alter the operation of the implanted device.

Further, U.S. Pat. No. 10,568,559 B2 relates to a method for determining a desired location at which to apply a neural therapy, the method comprising, implanting an array of electrodes mounted on a common paddle proximal to neural tissue, where a first plurality of electrodes in the array are configured to provide an electrical stimulus, and a second plurality of electrodes in the array are configured to internally measure neural compound action potential responses, applying a stimulus from the array which evokes a neural compound action potential response in the neural tissue proximal to the array using the first plurality of electrodes, obtaining a plurality of simultaneous respective internal measurements of the neural compound action potential response evoked by applying the stimulus using the second plurality of electrodes, the plurality of simultaneous respective internal measurements being obtained from respective distinct measurement amplifiers each connected to respective distinct electrodes of the second plurality of electrodes and determining from the plurality of internal measurements of the neural compound action potential response a neural sensitivity map of the area alongside the array and determining therefrom a desired location at which to apply a neural therapy in order to suppress undesired/adverse stimulation effects such as undesired paresthesia elicited by the neural therapy.

In addition, U.S. Pat. No. 9,713,720 discloses a neurostimulation system configured for providing therapy to a patient, comprises at least one implantable neurostimulation lead configured for being implanted adjacent target tissue of the patient, and an implantable neurostimulator configured for delivering electrical stimulation energy to the implantable neurostimulation leads in accordance with a set of stimulation parameters, and monitoring circuitry configured for taking at least one measurement indicative of a three-dimensional migration of the neurostimulation leads from a baseline position. The neurostimulation system further comprises at least one controller/processor configured for determining whether the three-dimensional migration of the neurostimulation leads from the baseline position has occurred based on the measurements, and, based on the determined three-dimensional migration, generating a new set of stimulation parameters, and reprogramming the implantable neurostimulator with the new set of stimulation parameters. Effectively, U.S. Pat. No. 9,713,720 proposes that an impedance measurement may be used to infer a lead position.

Further prior art relevant for the technical background of the present invention is provided by US 2013/0253299 A1, U.S. Pat. No. 9,636,497 B2 and by Yadav, A. P., Li, D. & Nicolelis, M. A. L.: "*A Brain to Spine Interface for Transferring Artificial Sensory Information*". Sci Rep 10, 900 (2020).

In the latter it is shown that rats are able to consistently discriminate 3 (and likely 4) distinct burst stimulation patterns applied to dorsal column of the spinal cord via modulation of the burst parameters: Pattern 1: 100 pulses at 333 Hz; Pattern 2:1 pulse; Pattern 3:100 pulses at 100 Hz; Pattern 4:5 bursts of 20 pulses each, with inter-burst frequency of 2 Hz and inter pulse frequency of 333 Hz. Moreover, the effects of stimulation patterns were also observed in the theta band (5 Hz-9.5 Hz) spectral power of local-field-potential, LFP, recordings in the motor cortex ($M_1$), somatosensory cortex ($S_1$), and striatum (STR) in response to stimulation patterns 1 & 2.

However, the methods, devices and systems provided by the prior art have various deficiencies. For instance, the systems and methods known from the prior art do not allow to perform on-line re-calibration of stimulation parameters or only to a very limited extend. In addition, consistency and long-term stability of desired artificial sensory perceptions/artificial sensations that are to be elicited in specific sensory cortex areas may not be ensured with the prior art systems, mainly because in the prior art this technical problem faced by CBI devices may not even arise or may not have the same importance as for CBI applications. In essence, several of the prior art systems discussed above utilize closed-loop methods for detecting neural responses to minimize the occurrence of certain reactions (such as paresthesias, pain etc.). To use an analogy, the prior art systems effectively function similar to audio speakers or headset systems that contain microphones which detect the emitted sound level and will automatically lower the volume if a threshold is reached, thereby protecting the user from unpleasant sensation/high volume sound.

It is thus a problem underlying the present invention to overcome such deficiencies of previous technologies by providing a novel autocalibration method for CBI devices and systems that allow on-line recalibration of stimulation parameters.

3. SUMMARY OF THE INVENTION

The above-mentioned problems are at least partially solved by an autocalibration method and computer program as specified by the independent claims. Exemplary embodiments of the present invention are specified in the dependent claims.

Generally, the present invention allows to implement closed-loop and on-line autocalibration of a CBI that is based on observing the excitation behavior/neural activation function of afferent sensory nerve fibers that provide a communication pathway to the brain of an individual. This approach is based on the insight that there exist strong correlations between the highly non-linear bioelectric response of an active stimulated afferent sensory nerve fiber or plurality of such fibers and a corresponding artificial sensory perception/artificial sensation elicited in a sensory cortex area of the individual. In loose analogy to standard candles in astronomy, this non-linear bioelectric response essentially serves as a fingerprint of the afferent sensory nerve fiber that may be measured and used for on-line recalibration of neurostimulation signal parameters for direct neurostimulation of afferent sensory axons (e.g. thalamocortical axons, afferent sensory axons of the brain stem or spinal cord and/or afferent sensory axons of the peripheral nervous system) targeting directly or indirectly (i.e. via multi-synaptic afferent pathways) sensory neurons in a target sensory cortex area. In this manner, long-term stability of highly specific, fine-grained, and multi-dimensional information transfer to the brain may be ensured.

More specifically, in a $1^{st}$ aspect, the present invention provides a method for self-calibrating a computer brain interface, CBI, device of an individual, comprising the following steps: choosing a set of test signal parameters, generating, based on the chosen set of test signal parameters, at least one neurostimulation test signal configured to elicit a bioelectric response in one or more afferent sensory nerve fibers, applying the generated neurostimulation test signal to the afferent sensory nerve fibers via a neurostimulation interface operably connected to or integrated with the CBI device, sensing, via the neurostimulation interface, one or more bioelectric responses of the one or more stimulated afferent sensory nerve fibers, determining, based on the sensed bioelectric responses, whether an excitation behavior of the stimulated afferent sensory nerve fibers with respect to the neurostimulation interface has changed, if the excitation behavior has changed, determining, based on the sensed bioelectric responses, a set of recalibrated neurostimulation signal parameters and operating the CBI device, using the recalibrated neurostimulation signal parameters, to communicate information to the individual, via neurostimulation of the one or more afferent sensory nerve fibers.

Throughout the present application the terms artificial sensation and artificial sensory perception are used interchangeably. Both terms indicate that an neural excitation pattern is generated in a population of sensory neurons in a sensory cortex area not in response to a sensory stimulus sensed by one of the natural sensory organs of a person (e.g. by mechanoreceptor cells, inner hair cells of the cochlea, rod cells of the retina, etc.) but artificially via direct neurostimulation of afferent sensory pathways using a neurostimulation interface.

According to a $2^{nd}$ aspect, in the $1^{st}$ aspect, the method may further comprise generating, based on the determined set of recalibrated signal parameters, a communication neurostimulation signal, configured to elicit an artificial sensation in a sensory cortex area of the individual via stimulating the one or more afferent sensory nerve fibers terminating in the specific sensory cortex area, wherein the artificial sensation is associated with a block of information to be communicated by the CBI device.

In this manner, consistency and long-term stability of the elicited artificial sensory perceptions that form the syntactic basis for sensory communication may be maintained regardless of tissue alterations, movement or migration of the neurostimulation electrodes relative to the stimulation target and/or changes in the electrical transfer function of the neurostimulation equipment. In essence, the described method thus provides an active compensation mechanism that ensures continuous optimal information transmission into the nervous system throughout changing factors (e.g. movement of electrodes relative to stimulation target) and states (e.g. changes of neural responsivity).

For instance, in a $3^{rd}$ aspect, in the $1^{st}$ or $2^{nd}$ aspect, determining the set of recalibrated neurostimulation signal parameters may comprise: comparing the sensed bioelectric responses to a set of reference bioelectric responses stored in a memory module of the CBI device or obtained via a communication interface of the CBI device.

In this manner, a precise characterization of the excitation behavior of the afferent sensory nerve fibers (e.g. obtained in a dedicated laboratory upon initial calibration of the CBI device and/or the neurostimulation interface) may serve as a reference for on-line recalibration, thereby improving the accuracy of recalibration.

For example, in a $4^{th}$ aspect, in the $3^{rd}$ aspect, the set of reference bioelectric responses may be associated with a set of artificial sensations that may be elicited by the CBI device via the neurostimulation interface in a sensory cortex area of the individual and that are associated with one or more blocks of information that may be communicated via the CBI device to the individual.

In a $5^{th}$ aspect, in the $3^{rd}$ or $4^{th}$ aspect, the method discussed above may further comprise determining the set of reference bioelectric responses based on one or more of the following: an initial or on-line calibration procedure involving the individual providing subjective feedback on artificial sensations elicited by a set of reference neurostimulation test signals; a plurality of reference calibration measurements performed on a plurality of individuals (e.g. a plurality including or not including the individual for whom the CBI and/or neurostimulation interface is to be calibrated) prior to determining the set of reference bioelectric responses for the individual; and an initial or online calibration procedure involving the individual performing a task with objectifiable outcomes that are supported by the operation of the CBI device and recording stimulation parameters and corresponding bioelectric responses that optimize performance of the task without recording subjective feedback by the individual.

For instance, during an initial calibration procedure conducted in a dedicated laboratory setting a set of reference neurostimulation test signals may be applied via the neurostimulation interface and bioelectric responses of the stimulate afferent sensory nerve fibers such as evoked compound action potentials may be measured (see FIG. 3a discussed in section 4. below). Additionally, the individual may provide, e.g. via a microphone, a graphical user interface or a smart phone application etc., subjective feedback on the type, locus, intensity, quality, etc. of the perceived artificial sensations elicited by the set of reference neurostimulation test signals. This subjective feedback may then be combined and correlated with the measured bioelectric response in order to obtain a mapping between a set of specific bioelectric response of the stimulated afferent sensory nerve fibers and a corresponding set of desired artificial sensations perceived by the individual.

Further, since the physiologic and functional structure of afferent sensory pathways such as afferent sensory nerve fibers of the spinal cord is stereotypical and strongly conserved across individuals a plurality of reference calibration measurements performed on a plurality of other individuals as described above, may be used for calibrating the CBI and/or neurostimulation interface of a new individual without having to perform a full initial calibration procedure.

In addition, for CBI devices whose operation is for instance directed to support or enhance an action or movement of the individual (e.g. a balance support CBI, a CBI improving gait, motor-coordination, etc.) it is even possible to perform initial calibration in an objective manner without requiring subjective feedback on perceived sensations. For instance, a person could be instructed, e.g. via smart phone application, to perform a set of calibration actions or movements that are supported by the operation of the CBI device, such as walking a certain distance in a straight line. While walking the CBI device could carry out an on-line reference calibration procedure where the CBI device records specific stimulation parameters and corresponding bioelectric responses that optimize the walking performance.

Accordingly, the present disclosure also provides a method for initial calibration of a computer brain interface, CBI, device of an individual, comprising the following steps: choosing a set of initial test signal parameters, generating, based on the chosen set of test signal parameters, at least one reference neurostimulation test signal configured to elicit a bioelectric response in one or more afferent sensory nerve fibers; applying the generated reference neurostimulation test signals to the afferent sensory nerve fibers via a neurostimulation interface operably connected to or integrated with the CBI device; sensing via the neurostimulation interface, one or more bioelectric responses of the one or more stimulated afferent sensory nerve fibers; obtaining a subjective or objective feedback signal associated with an artificial sensory perception elicited by the applied reference neurostimulation test signal; and correlating the chosen set of initial test signal parameters, the corresponding bioelectric responses and the corresponding elicited artificial sensory perceptions.

For instance, a subjective feedback may be obtained from a graphical user interface, e.g. provided by a smartphone application with which the individual inputs subjective feedback on artificial sensations elicited by the reference neurostimulation test signals. Objective feedback signals, on the other hand may be obtained from one or more sensor devices (e.g. accelerometers, LIDAR, gyroscope sensors, etc.) measuring quantities relating to the behavioral state of the individual.

Moreover, in a $6^{th}$ aspect, in any one of the $1^{st}$ to $5^{th}$ aspect, a plurality of different neurostimulation test signals may be generated and applied to the afferent sensory nerve fiber interleaved with a plurality of sensing periods for sensing corresponding bioelectric responses of the afferent sensory nerve fibers.

For instance, in a $7^{th}$ aspect, in the $6^{th}$ aspect, the plurality of different neurostimulation test signals are generated such that one or more test signal parameters are varied in a systematic manner in order to estimate a systematic dependence of the excitation behavior of the afferent sensory nerve fibers on the one or more systematically varied test signal parameters.

In this manner, even complex, multi-dimensional dependence of the excitation behavior of the one or more afferent sensory nerve fibers may be determined fast and efficiently without loss of accuracy.

In this context, in an $8^{th}$ aspect, in the $7^{th}$ aspect, it may be advantageous that the one or more test signal parameters are varied in form of an increasing or decreasing ramp and/or that the one or more signal parameters comprise one or more of the following: a spatial activation patter of the neurostimulation interface, a signal amplitude, an inter-pulse frequency, an inter-burst frequency, a pulse width, a wave form shape, a density of pulses within a burst, a signal polarity or a burst duration. In a similar manner, the test signal parameters might also be varied according to any of various known design-of-experiment (DOE) methodologies (e.g. methodologies as used when trying to understand the effect of multiple variables to optimize a chemical reaction/process.)

Further, in an $9^{th}$ aspect, in any one of the $1^{st}$ to $8^{th}$ aspect, determining the set of recalibrated neurostimulation signal parameters may comprise fitting a response function to a plurality of data points, wherein each data point comprises a set of test signal parameters and a corresponding bioelectric response level sensed by the CBI device; and/or determining the set of recalibrated neurostimulation signal parameters may comprise aggregating several bioelectric response recordings for the same chosen set of test signal parameters.

In this manner, recalibration may not require sampling the full, potentially multi-dimensional parameter space. Instead, known and/or previously derived functional dependencies of the excitation behavior of the one or more afferent sensory nerve fibers may be taken into account and measuring only a subset of data points (e.g. sparsely distributed throughout the parameter space) may be sufficient to obtain precisely recalibrated neurostimulation parameters suitable for neural communication via the CBI device.

In a $10^{th}$ aspect, in any one of the $1^{st}$ to $9^{th}$ aspect, the sensed bioelectric response may correspond to one or more extracellularly sensed action potentials or local field potentials or evoked compound action potentials (ECAPs) elicited by the at least one neurostimulation test signal in the afferent sensory nerve fibers.

Moreover, in an 11$^{th}$ aspect, in the 9$^{th}$ to 10$^{th}$ aspect, the response function may relate two or more different test signal parameters to an excitation threshold of the afferent sensory nerve fiber (e.g. an excitation threshold for eliciting a specific ECAP in the targeted afferent sensory nerve fibers etc.).

The present invention further provides, in a 12$^{th}$ aspect, a method for operating a CBI device to communicate information to an individual, comprising: transmitting a plurality of sensory messages to a sensory cortex area of the individual via stimulating one or more afferent sensory nerve fibers terminating in the sensory cortex area, and repeatedly carrying out the steps of the calibration method of any of the preceding claims 1-10 interleaved with transmitting of the sensory messages using the respective recalibrated neurostimulation signal parameters.

In this manner, the present invention enables a CBI device to constantly update and adapt its intrinsic stimulation parameter configuration without requiring human intervention or even laboratory-based recalibration.

The present invention also provides a computer program, comprising instructions for carrying out the method described above with respect to the 1$^{st}$ to 12$^{th}$ aspect, when being executed by processing and neurostimulation circuitry of a neurostimulation device or system.

The present invention further provides, in a 14$^{th}$ aspect, a CBI device, comprising one or more stimulation and sensing channels adapted to elicit and sense a bioelectric response of one or more afferent sensory nerve fiber terminating (e.g. mono- or multi-synaptically) in a sensory cortex area of an individual, and data and signal processing circuitry configured to carry out the method described above with respect to the 1$^{st}$ to 12$^{th}$ aspect.

Such a CBI device may further comprise a memory module operably connected to the data and signal processing circuitry storing a first mapping between one or more artificial sensations that may be elicited by the CBI device in one or more sensory cortex areas of the individual and one or more bioelectric responses; and/or storing a second mapping between a plurality of sets of neurostimulation signal parameters and a plurality of bioelectric responses of the one or more afferent sensory nerve fibers (e.g. recorded upon initial calibration and/or during on-line recalibration as outline above).

4. SHORT DESCRIPTION OF THE FIGURES

Figure 2:
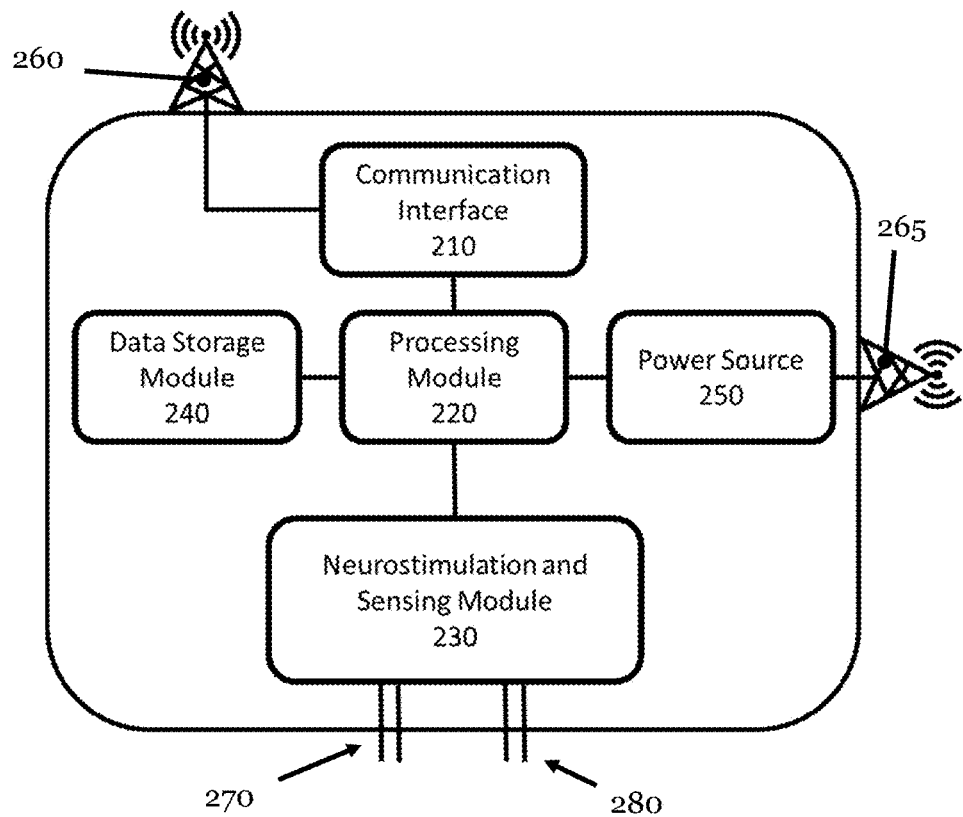
Figure 3A:
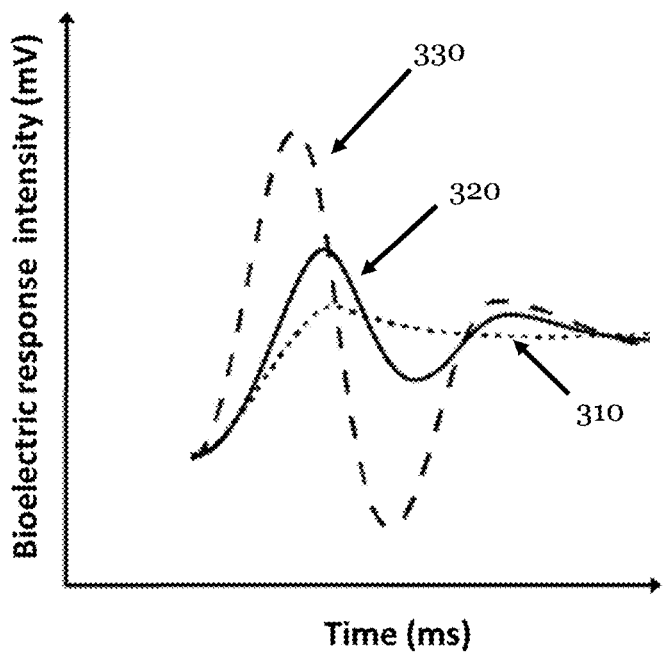
Figure 3B:
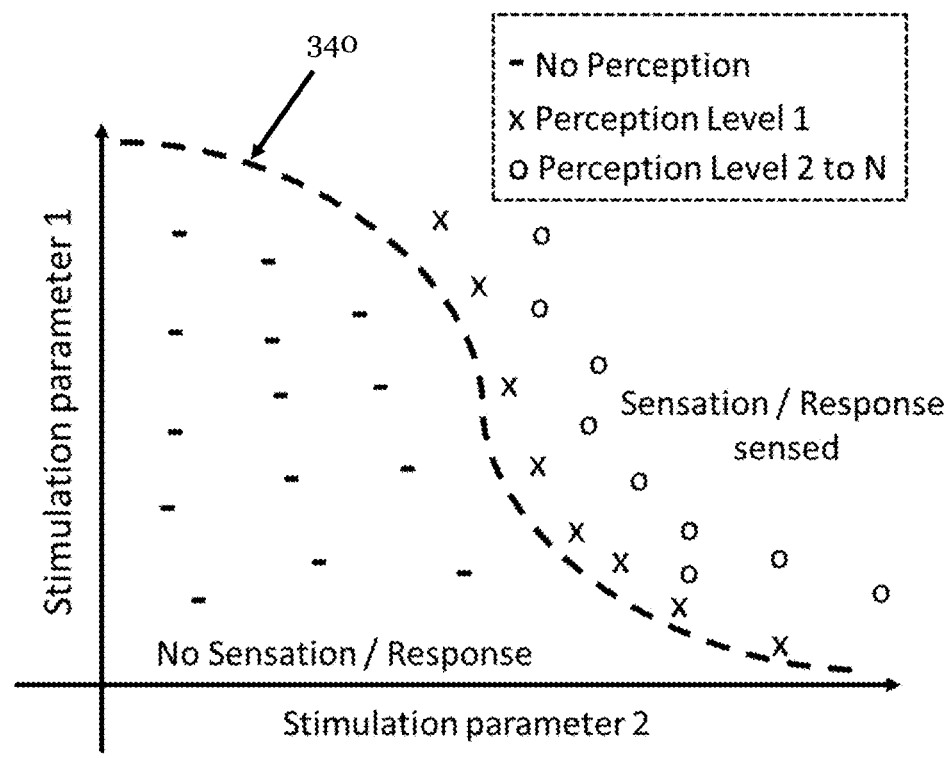
Figure 3C:
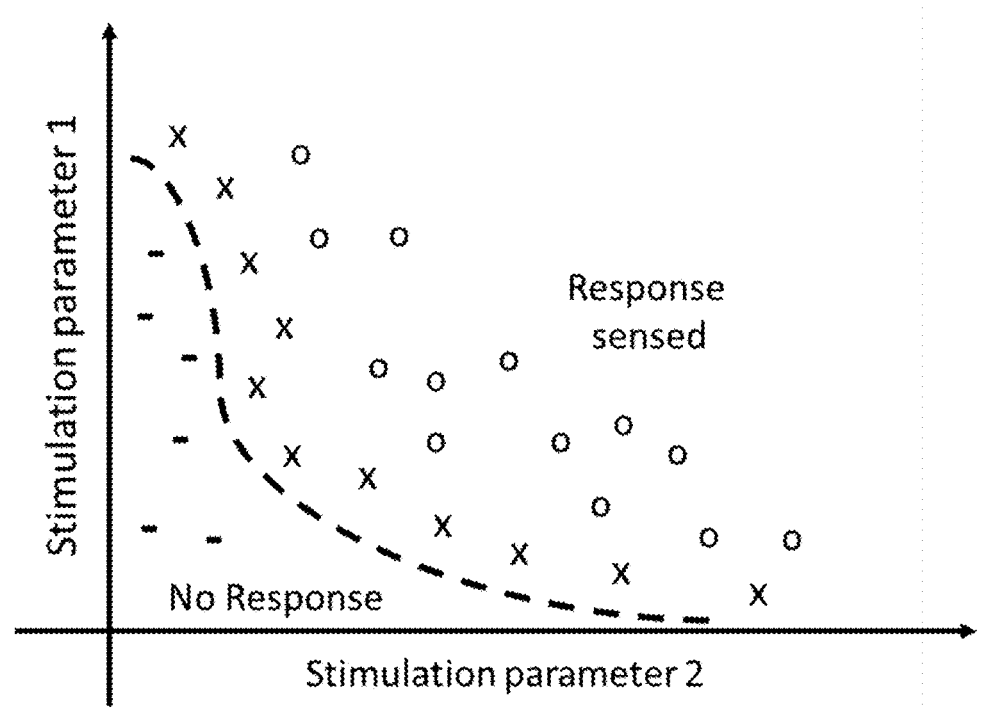
Figure 4:
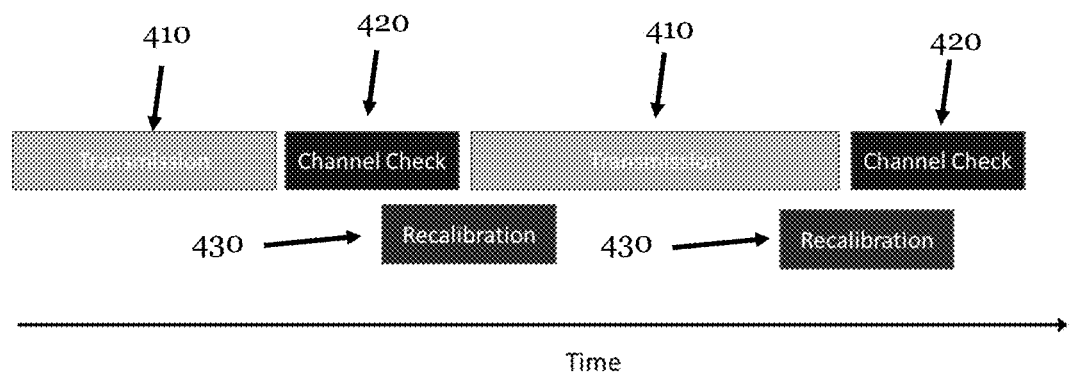
Figure 5:
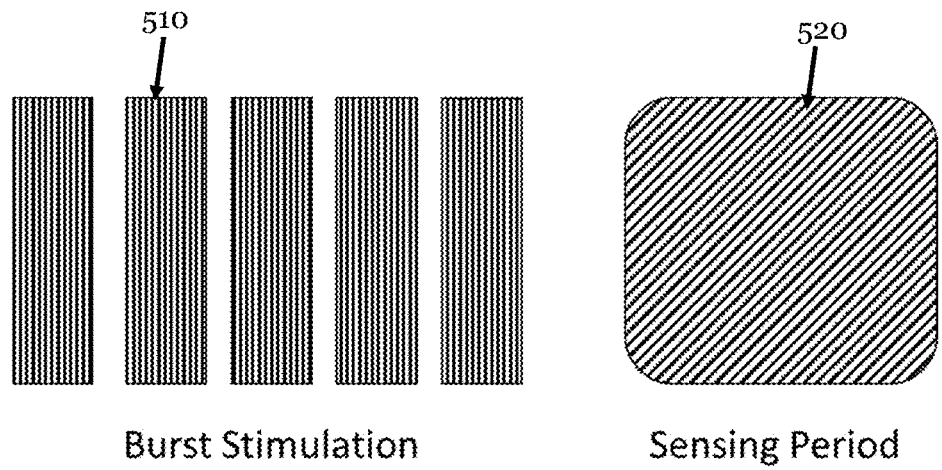
Figure 6:
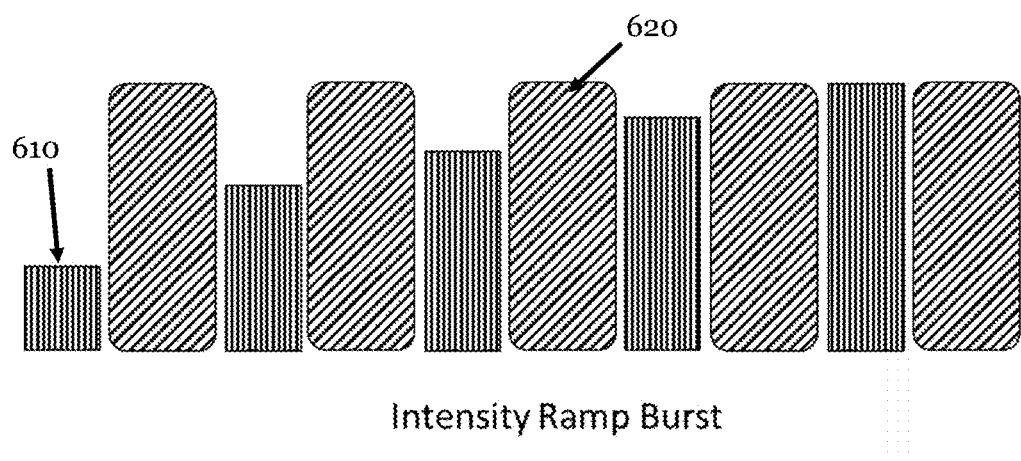
Figure 7:
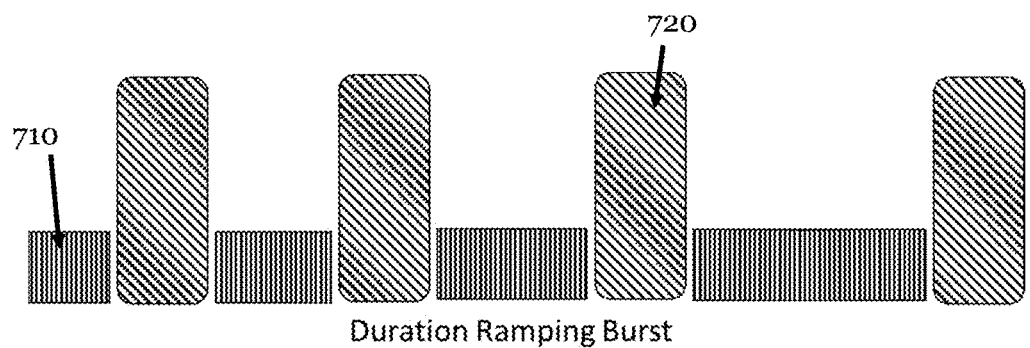
Figure 8:
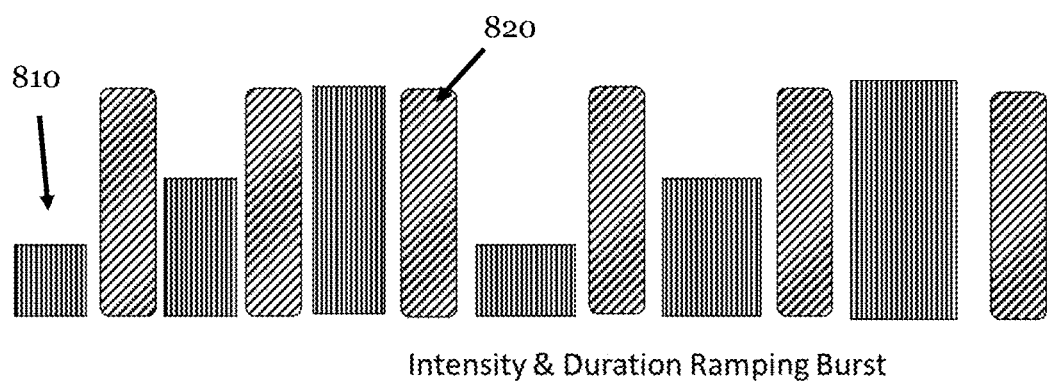
Figure 9:
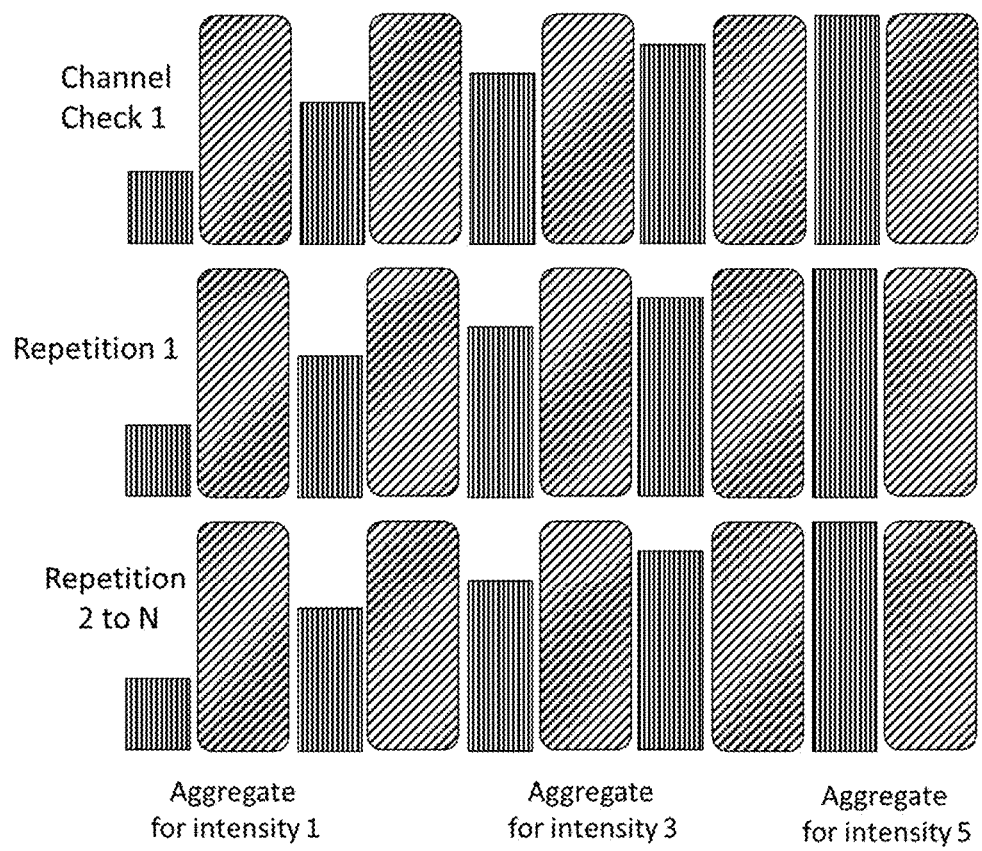

Various aspects of the present invention are described in more detail in the following by reference to the accompanying figures. These figures show:

FIG. 1 a diagram illustrating an individual being equipped with a CBI device according to an embodiment of the present invention;

FIG. 2 a functional block circuit diagram illustrating a CBI device according to an embodiment of the present invention;

FIG. 3a a diagram illustrating a set of bioelectric responses recorded from an afferent sensory nerve fiber bundle upon initial calibration of a neurostimulation interface driven by a CBI device according to an embodiment of the present invention;

FIG. 3b a diagram illustrating a plurality of systematic measurements of bioelectric responses of an afferent sensory nerve fiber depending on two different neurostimulation parameters recorded during initial calibration of a CBI device according to an embodiment of the present invention for characterizing the excitation behavior of the stimulated afferent sensory nerve fiber with respect to the neurostimulation interface driven by the CBI device;

FIG. 3c a diagram illustrating a change in the excitation behavior of afferent sensory nerve fibers with respect to a neurostimulation interface driven by a CBI device according to an embodiment of the present invention;

FIG. 4 a diagram illustrating the operation of a CBI device executing an on-line autocalibration method according to an embodiment of the present invention in an interleaved manner with actual information transmissions to the brain of an individual;

FIG. 5 a diagram illustrating a first example of a neurostimulation test signal and a corresponding bioelectric response sensing period executed as part of an autocalibration method according to an embodiment of the present invention;

FIG. 6 a diagram illustrating a second example of a neurostimulation test signal and corresponding bioelectric response sensing periods executed as part of an autocalibration method according to an embodiment of the present invention;

FIG. 7 a diagram illustrating a third example of a neurostimulation test signal and corresponding bioelectric response sensing periods executed as part of an autocalibration method according to an embodiment of the present invention;

FIG. 8 a diagram illustrating a fourth example of a neurostimulation test signal and corresponding bioelectric response sensing periods executed as part of an autocalibration method according to an embodiment of the present invention;

FIG. 9 a diagram illustrating a fifths example of a neurostimulation test signal and corresponding bioelectric response recordings executed as part of an autocalibration method according to an embodiment of the present invention;

5 DETAILED DESCRIPTION OF SOME EXEMPLARY EMBODIMENTS

In the following, some exemplary embodiments of the present invention are described in more detail, with reference to a CBI device that may be interfaced with neurostimulation electrodes such as spinal cord stimulation electrodes and/or DBS electrodes, e.g. via an intermediate neurostimulation device. However, the present invention may also be used with any other neurostimulation interface that is capable of stimulating afferent sensory axons of the central or peripheral nervous system targeting directly or indirectly a sensory cortex area of an individual.

While specific feature combinations are described in the following paragraphs with respect to the exemplary embodiments of the present invention, it is to be understood that not all features of the discussed embodiments have to be present for realizing the invention, which is defined by the subject matter of the claims. The disclosed embodiments may be modified by combining certain features of one embodiment with one or more technically and functionally compatible features of other embodiments. Specifically, the skilled person will understand that features, components and/or functional elements of one embodiment may be combined with technically compatible features, components and/or functional elements of any other embodiment of the present invention which is defined by the appended claims.

Moreover, the various modules of the devices and systems disclosed herein may for instance be implemented in hardware, software or a combination thereof. For instance, the various modules of the devices and systems disclosed herein may be implemented via application specific hardware components such as application specific integrated circuits, ASICs, and/or field programmable gate arrays, FPGAs, and/or similar components and/or application specific software modules being executed on multi-purpose data and signal processing equipment such as CPUs, DSPs and/or systems on a chip (SOCs) or similar components or any combination thereof.

For instance, the various modules of the CBI devices discussed herein above may be implemented on a multi-purpose data and signal processing device configured for executing application specific software modules and for communicating with various sensor devices and/or neurostimulation devices or systems via conventional wireless communication interfaces such as a NFC, a WIFI and/or a Bluetooth interface.

Alternatively, the various modules of the CBI devices discussed in the present application may also be part of an integrated neurostimulation apparatus, further comprising specialized electronic circuitry (e.g. neurostimulation signal generators, amplifiers etc.) for generating and applying the determined neurostimulation signals to a neurostimulation interface of the individual (e.g. a multi-contact electrode, a spinal cord stimulation electrode, peripheral sensory nerve stimulation electrode etc.).

As discussed above the present invention may be realized in situations where the perceptual channels of a general-purpose CBI are not calibrated via subject-experimenter interactions. Instead, the CBI stimulation parameters may be self-calibrated by tapping into the neural activity of the tissue in vicinity of the stimulation interface. For instance, the level of induced bioelectric activation may be measured by interleaving several special calibration test pulses in between the normal stream of communication stimuli.

In some examples, the special test waveforms are defined by modulating various aspect of the waveform in bursting mode. The modulated parameters of the waveform may include but are not limited to: a spatial activation pattern of the electrode contacts, an amplitude, an inter-pulse frequency, an inter-burst frequency, a pulse width, a wave-form shape (e.g. mono-phasic, biphasic with symmetric or with long active discharge period, multiphasic, etc.), a density of pulses within a burst or a burst duration. In an exemplary stimulation paradigm, a few symmetric pulses (e.g. in a range of 4-9 pulses) are delivered within short bursts (e.g. lasting 40 ms-60 ms) to convey information related to intensity of sensation. The intensity may then be varied at a second measurement loci point in time by changing density of pulses per burst while keeping pulse numbers constant i.e. shortening duration but increase intra-burst frequency and vice-versa.

For instance, neural recordings/sensing of bioelectric responses may take place by ramping stimulation signal bursts in repetition, aggregate frequency power pre- and post-pulse for each step of the ramp across repeated bursts then create differential response profile to pulses with varied intensity for the same purpose, so that the CBI device may estimate the neural excitation behavior of the stimulated afferent sensory nerve fibers by fitting a response function to the amplitude of the ECAP or theta frequency band of the ECAPs taking into account the response at every intensity increment. As stated above the excitation behavior may also be estimated not only by varying the amplitude of the burst in a ramp by also by changing other parameters of the stimulation such as frequency, pulse width, as well as the inter burst intervals, for example.

The estimated excitation behavior allows then to determine optimal stimulation parameters which are adequate to generate desired level of activity in the target tissue thereby stabilizing the intensity, locus and/or quality of artificial sensory perceptions in the targeted sensory cortex area. This may be achieved by determining the highest value parameter coefficients which crucially contribute to determination of sensation intensity.

FIG. 1 illustrates a person/individual 100 that is equipped with a CBI device as described in section 3 above. In the illustrated embodiment, the CBI is implemented via direct neurostimulation of afferent sensory nerve fibers in the spinal cord 106 via one or more multi-contact electrodes 104 driven by an IPG 102 that may be operatively connected to or integrated with a CBI device as disclosed herein.

For establishing a perceptual communication channel to the brain of the individual 100 the CBI device may be calibrated such that neurostimulation signals generated by the CBI device and applied via the IGP 102 and the multi-contact electrode 104 elicit one or more action potentials 108 in one or more afferent sensory nerve fibers of the spinal cord 106 targeting (e.g. via multi-synaptic afferent sensory pathways) one or more sensory cortex areas 110 of the individual where the one or more action potentials 108 generate artificial sensory perceptions that may be used to communicate with the individual 100. As discussed in detail in US 2020/0269049, fully incorporated herein by reference, artificial sensory perceptions that are elicited in a sensory cortex area (e.g. a sensory cortex area processing touch sensations on the left or right hand) may be associated with any kind of abstract information that is intelligible (i.e. consciously or subconsciously) by the individual.

FIG. 2 shows an exemplary CBI device according to an embodiment of the present invention. In this embodiment, the CBI device comprises an integrated neurostimulation and sensing module 230 (e.g. comprising a neuronal signal generator and an output amplifier as well as a sensing amplifier and an analog to digital converted) that is connected to a plurality of output signal leads 270 and a plurality of separate or identical sensing signal leads 280 that may be interfaced with a neurostimulation interface of the individual (e.g. a multi-contact spinal cord stimulation electrode such as the electrode 104 shown in FIG. 1). The CBI device may further comprise a communication antenna 260 operably connected to a communication interface module 210, configured for wireless communication (e.g. via NFC, Bluetooth, or a similar wireless communication technology).

The communication interface module 210 may be configured, for example, to receive one or more sensor signals from one or more sensors (not shown; e.g. acceleration signals obtained form an accelerometer etc.) and/or control information from a control device such as a remote control or a smart phone. The communication interface module 210 is operably connected to a data/signal processing module 220 configured to generate one or more neurostimulation signals and/or signal parameters (e.g. waveform, pulse shape, amplitude, frequency, burst count, burst duration etc.) for generating the one or more neurostimulation signals. For instance the processing module 220 may access a data storage module 240 configured to store a plurality of relations, specific for the individual, associating a plurality of neurostimulation signals (or parameters used for generating a plurality of neurostimulation signals) with a plurality of corresponding pieces of information to be communicated to the individual.

The generated neurostimulation signals and/or the signal parameters are input into the integrated neurostimulation and sensing module 230 that may be configured to process (e.g. modulate, switch, amplify, covert, rectify, multiplex, phase shift, etc.) the one or more neurostimulation signals generated by the processing module 220 or to generate the one or more neurostimulation signals based on the signal parameters provided by the processing module 220.

The generated and processed neurostimulation signals are then output by the neurostimulation and sensing module 230 and may be applied to one or more electric contacts of a neurostimulation electrode (e.g. a DBS electrode or spinal cord stimulation electrode as shown in FIG. 1) via output leads 270. The CBI device of FIG. 2 may also comprise a rechargeable power source 250 that, for instance may be wirelessly charged via a wireless charging interface 265.

As discussed above, the data/signal processing module 220 may be further configured to, e.g. in conjunction with the data storage module 240 and the neurostimulation and sensing module 230, to execute an on-line autocalibration method as discussed in section 3 above. For example, it may generate one or more neurostimulation test signals (for examples see FIGS. 5-9 below) configured to elicit a bioelectric response in one or more afferent sensory nerve fibers such as an evoked (compound) action potential in one or more afferent sensory nerve fibers of the spinal cord 106 shown in FIG. 1.

The neurostimulation test signal(s) (e.g. a combined intensity and burst-duration ramp; see FIG. 8) may then be applied via output stimulation leads 270 to a neurostimulation interface such as the most caudal contact 112 of the multi-contact electrode 104 shown in FIG. 1. The neurostimulation and sensing module 230 may then sense, via the neurostimulation interface (e.g. via the most rostral contact 114), a bioelectric response 108 of the stimulated afferent sensory nerve fiber of the spinal cord 106.

Based on the sensed bioelectric response, the excitation behavior of the stimulated afferent sensory nerve fibers with respect to the neurostimulation interface may then be estimated by the neurostimulation and sensing module 230 and/or the processing module 220. As discussed above (e.g. see section 3), based on the sensed bioelectric responses, a set of recalibrated neurostimulation signal parameters may then be determined and stored in the data storage module 240 for later use, e.g. for operating the CBI device to transmit information via the afferent sensory nerve fibers of the spinal cord 106 to a sensory cortex area 110 of the individual 100.

FIG. 3a illustrates exemplary reference bioelectric responses 310, 320, 330 (e.g. extracellularly sensed ECAPs) of a sub-population of afferent sensory nerve fibers (e.g. of the spinal cord 106; see FIG. 1) sensed and recorded upon initial calibration of a neurostimulation interface (e.g. the multi-contact spinal cord stimulation electrode 104 shown in FIG. 1) driven by a CBI device (see FIG. 2) according to an embodiment of the present invention. The illustrated bioelectric responses are sensed after neurostimulation using different sets of stimulation parameters such as different values for stimulus strength and duration. The bioelectric response 310 corresponds to a set of stimulation parameters that result in a sub-threshold stimulation of the targeted afferent sensory nerve fibers (see data points indicated with a "–" symbol in FIG. 3b and FIG. 3c). Consequently, no action potentials are elicited, and no artificial sensation may be elicited in the sensory cortex area(s), in which the targeted nerve fibers ultimately terminate. During initial calibration such a stimulation signal would thus not trigger individual to provide positive subjective feedback. The waveform of the bioelectric response 310 could then be stored in a memory module of the CBI device as a reference example of a sub-threshold bioelectric response that should be avoided when carrying out the autocalibration method as described above.

The bioelectric response 320 corresponds to a combination of stimulation parameters resulting in a supra-threshold stimulation of the targeted nerve fiber (see data points indicated with an "x" symbol in FIG. 3b and FIG. 3c) and eliciting a desired artificial sensory perception in a sensory cortex area of the individual, such as a mild tingling touch sensation on the left index finger that is clearly perceivable by the individual but is not unpleasant or painful. The waveform of the bioelectric response 320 could then be stored in a memory module of the CBI device as a reference example of a desired supra-threshold bioelectric response when carrying out the autocalibration method as described above.

Here it is important to note that that the terms "sub-threshold" &"supra-threshold" are tied to axonal activation (i.e. action potential generation in the targeted nerve fiber(s)) but are not necessarily tied to conscious perception. In other words, in some embodiments, a CBI device as disclosed herein may provide behavioral benefits (such as balance support or gait improvement cues) by generating supra-threshold spinal cord activation for which, however, the artificial sensations remain sub-conscious, e.g. after training and sematic calibration of the CBI device.

In such a configuration, the sematic calibration of the CBI device would be done conventionally with consciously reported sensations and objective behavioral tests and then one could gradually diminish the intensities (or different signal parameters) until the subject no longer reports any conscious perception but a behavioral benefit still persists. In other words, due to training (similar as when learning Braille script or Morse code) it is possible that the subject may not report the same conscious percepts anymore but may still intelligibly process the communicated information.

The bioelectric response 330 corresponds to a combination of stimulation parameters resulting in a supra-threshold stimulation of the targeted nerve fiber (see data points indicated with an "o" symbol in FIG. 3b and FIG. 3c) and eliciting a stronger (e.g. different or undesired) artificial sensory perception (e.g. too strong, wrong type of sensation, wrong locus of sensation, etc.) in a sensory cortex area of the individual, such as an unpleasant touch sensation on the abdomen of the individual. The waveform of the bioelectric response 330 could then be stored in a memory module of the CBI device as a reference example of a desired supra-threshold bioelectric response having an alternate sematic meaning or as an undesired supra-threshold bioelectric response when carrying out the autocalibration method as described above.

Naturally, several different bioelectric responses such as the response 320 may result in similar or essentially identical artificial sensations that may all be used for communicating the same block of information to the individual. The more response waveforms that are labeled with "desired/undesired" are stored in memory the better the on-line autocalibration method discussed above performs.

In order to serve as references for later use in an autocalibration method as discussed above, the stimulation parameters are thus associated, during initial calibration of the CBI device, to a threshold for eliciting an active, non-linear bioelectric response of the respective nerve fiber (e.g. an bioelectric response such as an ECAP having a specific intensity and signal shape). The excitation threshold of a nerve fiber may depend, inter alia, on the electric transfer function of the neurostimulation equipment, on the distance and relative orientation between stimulation contact and nerve fiber, the electric properties of the tissue surrounding the stimulation site, and the bioelectric properties (e.g. Na-ion and K-ion channel density) of the targeted nerve fiber etc.

By recording, upon initial calibration of the CBI device, the wave-form of bioelectric responses of the nerve fibers and by relating them activation threshold and a plurality of desired artificial sensations the CBI device may later be auto-calibrated in an on-line manner by observing the bioelectric responses of the nerve fiber alone without the need to record cortical activity patterns and/or without the individual participating in a laboratory-based calibration procedure.

FIG. 3b shows a diagram illustrating a plurality of systematic measurements of bioelectric responses of a subpopulation of afferent sensory nerve fibers depending on two different neurostimulation parameters recorded/sensed during initial calibration of a CBI device according to an embodiment of the present invention. By such a collection of measurements across a two or higher-dimensional stimulation parameter space the excitation behavior of the stimulated afferent sensory nerve fibers with respect to the neurostimulation interface driven by the CBI device may accurately be characterized.

For instance, data points are sampled from the parameter space and bioelectric response (e.g. ECAPs) are recorded. Some parameter combination elicit no responses (data points indicated with "–"), some elicit responses that the individual has reported as sensation intensity level 1 (data points indicated with "x") and some as sensation intensity level 2 or higher (data points indicated with "o"). It is simpler to retune the function if subjective perceptions of subjects are clearly mapped to the bio response signatures (e.g. during an initial calibration sessions) but this is not critically relevant. More important is that the dotted-line 340 (or a hyperplane for higher dimensional parameter spaces) delineates the dividing line between response and no response and this line is altered upon e.g. moving the implant or moving the spine in a certain way thereby changing the excitation behavior of the targeted afferent sensory nerve fiber.

Further, such functions may be calculated (e.g. to differentiate x & o intensity levels), so that shells of dividing lines may be pictured. In a certain sense they are also isolines—in the sense that alle parameters that trigger a response along that isoline trigger similar intensity responses. In the following a numerical example is given to illustrate the underlying concepts:

Example 1: Initial Calibration Session 0.5 mA; 500 ms burst duration: No Subjective Response/ No ECAP
2.5 mA; 500 ms burst duration: No Subjective Response/ Weak ECAP For example, such bioelectric responses may be associated during a sematic training session with a too weak stimulation that should be avoided. Accordingly, prior to re-calibration using the autocalibration method described above, this combination of stimulation parameters will not be used by the CBI device.

2.5 mA; 1000 ms burst duration: Response-Intensity weak perceived/Middle ECAP

For example, such a bioelectric response may be associated during a sematic training session with a piece/block of information to be communicated via the CBI device (e.g. the letter "A").

3.5 mA; 500 ms burst duration: Response—Intensity middle perceived/Strong ECAP

For example, such a bioelectric response may be associated during a sematic training session with a further piece/ block of information to be communicated via the CBI device (e.g. the letter "B").

3.5 mA; 1000 ms burst duration: Response-Intensity very strong perceived/Very Strong ECAP.

For example, such a bioelectric response may be associated during a sematic training session with an unpleasant artificial sensation to be avoided. Accordingly, prior to re-calibration using the autocalibration method described above, this combination of stimulation parameters will not be used by the CBI device.

FIG. 3c shows a diagram illustrating a change in the excitation behavior of the afferent sensory nerve fibers on which the initial calibration procedure resulting in FIG. 3a was performed. For instance, in this example, the position of the test signal stimulation contact moved with respect to the targeted afferent sensory nerve fiber. In the shown example, the dotted delimiting line 304 shifted towards the origin of the diagram as compare to the reference calibration procedure of FIG. 3b. In such a configuration, not changing stimulation parameters may well lead to an overstimulation of the targeted afferent sensory nerve fiber thereby degrading the quality of the corresponding perceptual communication channel.

However, the present invention allows, based on the reference bioelectric responses recorded for FIG. 3b, to recalibrate stimulation parameters (e.g. intensity and/or pulse duration, etc.) and thereby maintain the quality of the corresponding perceptual communication channel.

FIG. 4 shows an exemplary sequence of operation of a CBI device executing an on-line auto-calibration method according to an embodiment of the present invention in an interleaved manner with actual information transmissions to the brain of an individual. In this automated routine channel checks are interleaved with blocks of information transmission. Specifically, channel check periods 420 are interleaved with data transmission periods 420. Each channel check period 420 involves application of neurostimulation test signals and recording of a bioelectric response of the stimulated afferent sensory nerve fiber as discussed above. For instance, the examplary test signal—sensing sequences illustrated in FIGS. 5-9 may be used during such a channel check period 420.

Based on the sensed bioelectric response of the stimulated afferent sensory nerve fiber(s) a current activation function of the nerve fiber may be determined and compared to a reference activation function (see FIG. 4). If deviations from the reference activation function(s) are detected stimulation parameters may be recalibrated 43o. For instance, a set of recalibrated stimulation parameters (intensity, duration, pulse width, etc.) may be determined and then be used for a subsequent data transmission 410. In this manner, the intensity, quality, and/or locus of the corresponding artificial sensory perceptions may be stabilized. For instance, the present excitation behavior (see FIG. 3c above) may be estimated by utilizing bioelectric response measurements using at least two types of stimulation parameters such as the illustrated intensity and pulse duration.

The activation curve may however include other modalities or other dimensions (e.g. multi-dimensional activation curves). Importantly, a full re-sampling of the activation curve is not absolutely necessary since in many configurations a sparse sampling approach indicating a rheobase and chronaxie values would be enough to estimate the activation function without having to move through parameter space in brute force. As a result, the properties such as the channel bandwidth of the corresponding perceptual communication channel may be maintained even in normally behaving subjects during a broad range of daily activities.

FIG. 5 illustrates a test signal/recording configuration where the CBI device delivers (e.g. via a neurostimulation module; see FIG. 2) or commands an implanted stimulator to deliver whole bursts of test stimuli then waits for detection and recording of the induced bioelectric responses (e.g. action potentials, ECAPs, etc.) after the last pulse stimuli is applied. In this first example, stimulation parameters during burst stimulation 510 remain constant and bioelectric response (e.g. ECAP) measurement 520 takes place after the last pulse iteration within the burst.

FIG. 6 shows a test signal/recording sequence where the intensity of the neurostimulation test signal 610 is ramped and bioelectric response (e.g. ECAP) measurement 620 takes place after each pulse iteration within the burst.

FIG. 7 shows a test signal/recording sequence where the intensity of the neurostimulation test signal 710 is kept constant and the pulse duration is ramped. As in FIG. 6 bioelectric response (e.g. ECAP) measurement 720 takes place after each pulse iteration 710 within the burst.

FIG. 8 shows a combined intensity and pulse duration ramp, that for instance may be used to efficiently estimate a two-dimensional activation function (e.g. see FIGS. 3b and 3c). As in FIG. 6 and FIG. 7 bioelectric response (e.g. ECAP) measurement 820 takes place after each pulse iteration 810 within the burst sequence.

FIG. 9 illustrates how averaging across multiple channel check sequences may improve data quality and thus make the estimation of the current activation function more precise and noise tolerant.

The invention claimed is:

1. A method for self-calibrating a computer brain interface, CBI, device of an individual, the method comprising:
   selecting a set of test signal parameters;
   generating, based on the selected set of test signal parameters, at least one neurostimulation test signal configured to elicit a bioelectric response in one or more afferent sensory nerve fibers;
   applying the generated neurostimulation test signal to the afferent sensory nerve fibers via a neurostimulation interface operably connected to or integrated with the CBI device;
   sensing via the neurostimulation interface, one or more bioelectric responses of the one or more stimulated afferent sensory nerve fibers;
   determining, based on the sensed bioelectric responses, whether an excitation behavior of the stimulated afferent sensory nerve fibers with respect to the neurostimulation interface has changed;
   when the excitation behavior has changed, determining, based on the sensed bioelectric responses, a set of recalibrated neurostimulation signal parameters, wherein determining the set of recalibrated neurostimulation signal parameters comprises comparing the sensed bioelectric responses to a set of reference bioelectric responses stored in a memory module of the CBI device or obtained via a communication interface of the CBI device; and
   operating the CBI device, using the recalibrated neurostimulation signal parameters, to communicate information to the individual via neurostimulation of the one or more afferent sensory nerve fibers.

2. The method of claim 1, further comprising:
   generating, based on the determined set of recalibrated signal parameters, a communication neurostimulation signal, configured to elicit an artificial sensation in a sensory cortex area via stimulating the one or more afferent sensory nerve fiber terminating in the specific sensory cortex area,
   wherein the artificial sensation is associated with a block of information to be communicated by the CBI device.

3. The method of claim 1, wherein determining the set of recalibrated neurostimulation signal parameters comprises:
   comparing the sensed bioelectric responses to a set of reference bioelectric responses stored in a memory module of the CBI device or obtained via a communication interface of the CBI device.

4. The method of claim 3,
   wherein the set of reference bioelectric responses is associated with a set of artificial sensations that can be elicited by the CBI device via the neurostimulation m interface in a sensory cortex area of the individual and that are associated with one or more blocks of information that can be communicated via the CBI device to the individual.

5. The method of claim 3, further comprising:
   determining the set of reference bioelectric responses based on one or more of:
   an initial or on-line calibration procedure involving the individual providing subjective feedback on artificial sensations elicited by a set of reference neurostimulation test signals;
   a plurality of reference calibration measurements performed on a plurality of individuals prior to determining the set of reference bioelectric responses for the individual; and
   an initial or online calibration procedure involving the individual performing one or more tasks with objectifiable outcomes that are supported by the operation of the CBI device and recording stimulation parameters and corresponding bioelectric responses that optimize performance of the task without recording subjective feedback by the individual.

6. The method of claim 1,
   wherein a plurality of different neurostimulation test signals is generated and applied to the afferent sensory nerve fibers interleaved with a plurality of sensing periods of corresponding bioelectric responses of the afferent sensory nerve fibers.

7. The method of claim 6,
   wherein the plurality of different neurostimulation test signals is generated such that one or more test signal parameters are varied in a systematic manner in order to estimate a systematic dependence of the excitation behavior of the afferent sensory nerve fibers on the one or more systematically varied test signal parameters.

8. The method of claim 7,
   wherein the one or more test signal parameters are varied in form of an increasing or decreasing ramp, and/or
   wherein the one or more signal parameters comprise one or more of the following:

a spatial activation pattern of the neurostimulation interface,
a signal amplitude,
an inter-pulse frequency,
an inter-burst frequency,
a pulse width,
a wave form shape,
a density of pulses within a burst,
signal polarity, and
a burst duration.

9. The method of claim 1,
wherein determining the set of recalibrated neurostimulation signal parameters comprises fitting a response function to a plurality of data points, wherein each data point comprises a set of test signal parameters and a corresponding bioelectric response level sensed by the CBI device; and
wherein determining the set of recalibrated neurostimulation signal parameters comprises aggregating several bioelectric response recordings for the selected set of test signal parameters.

10. The method of claim 1,
wherein the sensed bioelectric responses correspond to one or more of:
one or more extracellularly recorded action potentials;
local field potentials; and
evoked compound action potentials elicited by the at least one neurostimulation test signal.

11. The method of claim 10, wherein the response function relates two or more different test signal parameters to an excitation threshold of the afferent sensory nerve fiber.

12. The method of claim 1, the method further comprising:
repeating the method for self-calibrating the CBI device to obtain updated sets of recalibrated neurostimulation signal parameters; and
communicating information to the individual via neurostimulation of the one or more afferent sensory nerve fibers using the updated sets of recalibrated neurostimulation signal parameters.

13. A computer program comprising instructions executable by a processor and neurostimulation circuitry of a neurostimulation device to:
select a set of test signal parameters;
generate, based on the selected set of test signal parameters, at least one neurostimulation test signal configured to elicit a bioelectric response in one or more afferent sensory nerve fibers;
apply the generated neurostimulation test signal to the afferent sensory nerve fibers via a neurostimulation interface operably connected to or integrated with the neurostimulation device;
sense via the neurostimulation interface, one or more bioelectric responses of the one or more stimulated afferent sensory nerve fibers;
determine, based on the sensed bioelectric responses, whether an excitation behavior of the stimulated afferent sensory nerve fibers with respect to the neurostimulation interface has changed;
when the excitation behavior has changed, determine, based on the sensed bioelectric responses, a set of recalibrated neurostimulation signal parameters; and
operate the neurostimulation device, using the recalibrated neurostimulation signal parameters, to communicate information to the individual via neurostimulation of the one or more afferent sensory nerve fibers.

14. The computer program of claim 13, wherein the instructions are further executable to cause the neurostimulation device to:
generate, based on the determined set of recalibrated signal parameters, a communication neurostimulation signal, configured to elicit an artificial sensation in a sensory cortex area via stimulating the one or more afferent sensory nerve fiber terminating in the specific sensory cortex area,
wherein the artificial sensation is associated with a block of information to be communicated by the neurostimulation device.

15. The computer program of claim 13, wherein in determining the set of recalibrated neurostimulation signal parameters, the instructions are executable to cause the neurostimulation device to:
compare the sensed bioelectric responses to a set of reference bioelectric responses stored in a memory module of the neurostimulation device or obtained via a communication interface of the neurostimulation device.

16. The computer program of claim 15,
wherein the set of reference bioelectric responses is associated with a set of artificial sensations that can be elicited by the neurostimulation device via the neurostimulation interface in a sensory cortex area of the individual and that are associated with one or more blocks of information that can be communicated via the neurostimulation device to the individual.

17. A computer-brain-interface, CBI, device, comprising:
a neurostimulation interface comprising one or more stimulation and recording channels adapted to elicit and record a bioelectric response of one or more afferent sensory nerve fibers terminating in a sensory cortex area of an individual; and
data and signal processing circuitry, wherein the CBI device is configured to:
select a set of test signal parameters;
generate, based on the selected set of test signal parameters, at least one neurostimulation test signal configured to elicit the bioelectric response in the one or more afferent sensory nerve fibers;
apply the generated neurostimulation test signal to the afferent sensory nerve fibers via the neurostimulation interface; and
sense, by the neurostimulation interface, one or more bioelectric responses of the one or more stimulated afferent sensory nerve fibers;
determine, based on the sensed bioelectric responses, whether an excitation behavior of the stimulated afferent sensory nerve fibers with respect to the neurostimulation interface has changed;
when the excitation behavior has changed, determine, based on the sensed bioelectric responses, a set of recalibrated neurostimulation signal parameters; and
using the neurostimulation interface, communicate information to the individual using the recalibrated neurostimulation signal parameters via neurostimulation of the one or more afferent sensory nerve fibers.

18. The CBI device of claim 17, further comprising
a memory module operably connected to the data and signal processing circuitry, wherein the memory stores one or both of:
a first mapping between one or more artificial sensations that can be elicited by the CBI device in one or more sensory cortex areas of the individual and one or more bioelectric responses; and a second mapping between a plurality of sets of neurostimulation signal parameters and a plurality of bioelectric responses of the one or more afferent sensory nerve fibers.

19. The CBI device of claim 17, wherein the CBI device is further configured to:

determine the set of reference bioelectric responses based on one or more of:

an initial or on-line calibration procedure involving the individual providing subjective feedback on artificial sensations elicited by a set of reference neurostimulation test signals;

a plurality of reference calibration measurements performed on a plurality of individuals prior to determining the set of reference bioelectric responses for the individual; and an initial or online calibration procedure involving the individual performing one or more tasks with objectifiable outcomes that are supported by the operation of the CBI device and recording stimulation parameters and corresponding bioelectric responses that optimize performance of the task without recording subjective feedback by the individual.

20. The CBI device of claim 17, wherein a plurality of different neurostimulation test signals is generated and applied to the afferent sensory nerve fibers interleaved with a plurality of sensing periods of corresponding bioelectric responses of the afferent sensory nerve fibers.

* * * * *

UNITED STATES PATENT AND TRADEMARK OFFICE
CERTIFICATE OF CORRECTION

PATENT NO. : 12,214,202 B2
APPLICATION NO. : 17/224953
DATED : February 4, 2025
INVENTOR(S) : Bálint Várkuti et al.

It is certified that error appears in the above-identified patent and that said Letters Patent is hereby corrected as shown below:

In the Claims

Replace Column 15, Line 44-Column 19, Line 31, (approx.) with attached Claims:
1. A method for self-calibrating a computer brain interface, CBI, device of an individual, the method comprising:
    selecting a set of test signal parameters;
    generating, based on the selected set of test signal parameters, at least one neurostimulation test signal configured to elicit a bioelectric response in one or more afferent sensory nerve fibers;
    applying the generated neurostimulation test signal to the afferent sensory nerve fibers via a neurostimulation interface operably connected to or integrated with the CBI device;
    sensing via the neurostimulation interface, one or more bioelectric responses of the one or more stimulated afferent sensory nerve fibers;
    determining, based on the sensed bioelectric responses, whether an excitation behavior of the stimulated afferent sensory nerve fibers with respect to the neurostimulation interface has changed;
    when the excitation behavior has changed, determining, based on the sensed bioelectric responses, a set of recalibrated neurostimulation signal parameters, wherein determining the set of recalibrated neurostimulation signal parameters comprises comparing the sensed bioelectric responses to a set of reference bioelectric responses stored in a memory module of the CBI device or obtained via a communication interface of the CBI device; and
    operating the CBI device, using the recalibrated neurostimulation signal parameters, to communicate information to the individual via neurostimulation of the one or more afferent sensory nerve fibers.

2. The method of claim 1, further comprising:
    generating, based on the determined set of recalibrated signal parameters, a communication Signed and Sealed this
Third Day of February, 2026

John A. Squires
*Director of the United States Patent and Trademark Office* neurostimulation signal, configured to elicit an artificial sensation in a sensory cortex area via stimulating the one or more afferent sensory nerve fiber terminating in the specific sensory cortex area, wherein the artificial sensation is associated with a block of information to be communicated by the CBI device.

3. The method of claim 1, wherein the set of reference bioelectric responses is associated with a set of artificial sensations that can be elicited by the CBI device via the neurostimulation interface in a sensory cortex area of the individual and that are associated with one or more blocks of information that can be communicated via the CBI device to the individual.

4. The method of claim 1, further comprising:

determining the set of reference bioelectric responses based on one or more of:

an initial or on-line calibration procedure involving the individual providing subjective feedback on artificial sensations elicited by a set of reference neurostimulation test signals;

a plurality of reference calibration measurements performed on a plurality of individuals prior to determining the set of reference bioelectric responses for the individual; and an initial or online calibration procedure involving the individual performing one or more tasks with objectifiable outcomes that are supported by the operation of the CBI device and recording stimulation parameters and corresponding bioelectric responses that optimize performance of the task without recording subjective feedback by the individual.

5. A method for self-calibrating a computer brain interface, CBI, device of an individual, the method comprising:

selecting a set of test signal parameters;

generating, based on the selected set of test signal parameters, at least one neurostimulation test signal configured to elicit a bioelectric response in one or more afferent sensory nerve fibers;

applying the generated neurostimulation test signal to the afferent sensory nerve fibers via a neurostimulation interface operably connected to or integrated with the CBI device;

sensing via the neurostimulation interface, one or more bioelectric responses of the one or more stimulated afferent sensory nerve fibers;

determining, based on the sensed bioelectric responses, whether an excitation behavior of the stimulated afferent sensory nerve fibers with respect to the neurostimulation interface has changed;

when the excitation behavior has changed, determining, based on the sensed bioelectric responses, a set of recalibrated neurostimulation signal parameters; and operating the CBI device, using the recalibrated neurostimulation signal parameters, to communicate information to the individual via neurostimulation of the one or more afferent sensory nerve fibers, wherein a plurality of different neurostimulation test signals is generated and applied to the afferent sensory nerve fibers interleaved with a plurality of sensing periods of corresponding bioelectric responses of the afferent sensory nerve fibers.

CERTIFICATE OF CORRECTION (continued)
U.S. Pat. No. 12,214,202 B2

6. The method of claim 5,
    wherein the plurality of different neurostimulation test signals is generated such that one or more test signal parameters are varied in a systematic manner in order to estimate a systematic dependence of the excitation behavior of the afferent sensory nerve fibers on the one or more systematically varied test signal parameters.

7. The method of claim 6,
    wherein the one or more test signal parameters are varied in form of an increasing or decreasing ramp and/or
    wherein the one or more signal parameters comprise one or more of the following:
        a spatial activation pattern of the neurostimulation interface,
        a signal amplitude,
        an inter-pulse frequency,
        an inter-burst frequency,
        a pulse width,
        a wave form shape,
        a density of pulses within a burst,
        signal polarity, and
        a burst duration.

8. A method for self-calibrating a computer brain interface, CBI, device of an individual, the method comprising:
    selecting a set of test signal parameters;
    generating, based on the selected set of test signal parameters, at least one neurostimulation test signal configured to elicit a bioelectric response in one or more afferent sensory nerve fibers;
    applying the generated neurostimulation test signal to the afferent sensory nerve fibers via a neurostimulation interface operably connected to or integrated with the CBI device;
    sensing via the neurostimulation interface, one or more bioelectric responses of the one or more stimulated afferent sensory nerve fibers;
    determining, based on the sensed bioelectric responses, whether an excitation behavior of the stimulated afferent sensory nerve fibers with respect to the neurostimulation interface has changed;
    when the excitation behavior has changed, determining, based on the sensed bioelectric responses, a set of recalibrated neurostimulation signal parameters; and
    operating the CBI device, using the recalibrated neurostimulation signal parameters, to communicate information to the individual via neurostimulation of the one or more afferent sensory nerve fibers,
    wherein determining the set of recalibrated neurostimulation signal parameters comprises fitting a response function to a plurality of data points, wherein each data point comprises a set of test signal parameters and a corresponding bioelectric response level sensed by the CBI device; and
    wherein determining the set of recalibrated neurostimulation signal parameters comprises aggregating several bioelectric response recordings for the selected set of test signal parameters.

CERTIFICATE OF CORRECTION (continued)
U.S. Pat. No. 12,214,202 B2

9. A method for self-calibrating a computer brain interface, CBI, device of an individual, the method comprising:

selecting a set of test signal parameters;

generating, based on the selected set of test signal parameters, at least one neurostimulation test signal configured to elicit a bioelectric response in one or more afferent sensory nerve fibers;

applying the generated neurostimulation test signal to the afferent sensory nerve fibers via a neurostimulation interface operably connected to or integrated with the CBI device;

sensing via the neurostimulation interface, one or more bioelectric responses of the one or more stimulated afferent sensory nerve fibers, wherein the sensed bioelectric responses correspond to one or more of:

one or more extracellularly recorded action potentials;

local field potentials; and evoked compound action potentials elicited by the at least one neurostimulation test signal;

determining, based on the sensed bioelectric responses, whether an excitation behavior of the stimulated afferent sensory nerve fibers with respect to the neurostimulation interface has changed;

when the excitation behavior has changed, determining, based on the sensed bioelectric responses, a set of recalibrated neurostimulation signal parameters; and operating the CBI device, using the recalibrated neurostimulation signal parameters, to communicate information to the individual via neurostimulation of the one or more afferent sensory nerve fibers.

10. The method of claim 9, wherein the response function relates two or more different test signal parameters to an excitation threshold of the afferent sensory nerve fiber.

11. A method for self-calibrating a computer brain interface, CBI, device of an individual, the method comprising:

selecting a set of test signal parameters;

generating, based on the selected set of test signal parameters, at least one neurostimulation test signal configured to elicit a bioelectric response in one or more afferent sensory nerve fibers;

applying the generated neurostimulation test signal to the afferent sensory nerve fibers via a neurostimulation interface operably connected to or integrated with the CBI device;

sensing via the neurostimulation interface, one or more bioelectric responses of the one or more stimulated afferent sensory nerve fibers;

determining, based on the sensed bioelectric responses, whether an excitation behavior of the stimulated afferent sensory nerve fibers with respect to the neurostimulation interface has changed;

when the excitation behavior has changed, determining, based on the sensed bioelectric responses, a set of recalibrated neurostimulation signal parameters; and operating the CBI device, using the recalibrated neurostimulation signal parameters, to communicate information to the individual via neurostimulation of the one or more afferent sensory nerve fibers, repeating the method for self-calibrating the CBI device to obtain updated sets of recalibrated neurostimulation signal parameters; and communicating information to the individual via neurostimulation of the one or more afferent sensory nerve fibers using the updated sets of recalibrated neurostimulation signal parameters.

12. A non-transitory computer-readable memory medium comprising program instructions, wherein the program instructions are executable by a processor and neurostimulation circuitry of a neurostimulation device to:

select a set of test signal parameters;

generate, based on the selected set of test signal parameters, at least one neurostimulation test signal configured to elicit a bioelectric response in one or more afferent sensory nerve fibers;

apply the generated neurostimulation test signal to the afferent sensory nerve fibers via a neurostimulation interface operably connected to or integrated with the neurostimulation device;

sense via the neurostimulation interface, one or more bioelectric responses of the one or more stimulated afferent sensory nerve fibers;

determine, based on the sensed bioelectric responses, whether an excitation behavior of the stimulated afferent sensory nerve fibers with respect to the neurostimulation interface has changed;

when the excitation behavior has changed, determine, based on the sensed bioelectric responses, a set of recalibrated neurostimulation signal parameters, wherein in determining the set of recalibrated neurostimulation signal parameters, the program instructions are executable to cause the neurostimulation device to:

compare the sensed bioelectric responses to a set of reference bioelectric responses stored in a memory module of the neurostimulation device or obtained via a communication interface of the neurostimulation device; and operate the neurostimulation device, using the recalibrated neurostimulation signal parameters, to communicate information to the individual via neurostimulation of the one or more afferent sensory nerve fibers.

13. The non-transitory computer-readable memory medium of claim 12, wherein the program instructions are further executable to cause the neurostimulation device to:

generate, based on the determined set of recalibrated signal parameters, a communication neurostimulation signal, configured to elicit an artificial sensation in a sensory cortex area via stimulating the one or more afferent sensory nerve fiber terminating in the specific sensory cortex area, wherein the artificial sensation is associated with a block of information to be communicated by the neurostimulation device.

14. The non-transitory computer-readable memory medium of claim 12, wherein the set of reference bioelectric responses is associated with a set of artificial sensations that can be elicited by the neurostimulation device via the neurostimulation interface in a sensory cortex area of the individual and that are associated with one or more blocks of information that can be communicated via the neurostimulation device to the individual.

15. The non-transitory computer-readable memory medium of claim 12, wherein determining the set of reference bioelectric responses is performed based on one or more of:

an initial or on-line calibration procedure involving the individual providing subjective feedback on artificial sensations elicited by a set of reference neurostimulation test signals;

a plurality of reference calibration measurements performed on a plurality of individuals prior to determining the set of reference bioelectric responses for the individual; and an initial or online calibration procedure involving the individual performing one or more tasks with objectifiable outcomes that are supported by the operation of the CBI device and recording stimulation parameters and corresponding bioelectric responses that optimize performance of the task without recording subjective feedback by the individual.

16. A computer brain interface (CBI) device, comprising:

neurostimulation circuitry; and a processor coupled to the neurostimulation circuitry, wherein the CBI device is configured to:

select a set of test signal parameters;

generate, based on the selected set of test signal parameters, at least one neurostimulation test signal configured to elicit a bioelectric response in one or more afferent sensory nerve fibers;

apply the generated neurostimulation test signal to the afferent sensory nerve fibers via a neurostimulation interface operably connected to or integrated with the CBI device;

sense via the neurostimulation interface, one or more bioelectric responses of the one or more stimulated afferent sensory nerve fibers;

determine, based on the sensed bioelectric responses, whether an excitation behavior of the stimulated afferent sensory nerve fibers with respect to the neurostimulation interface has changed;

when the excitation behavior has changed, determine, based on the sensed bioelectric responses, a set of recalibrated neurostimulation signal parameters, wherein in determining the set of recalibrated neurostimulation signal parameters, the CBI device is configured to:

compare the sensed bioelectric responses to a set of reference bioelectric responses stored in a memory module of the CBI device or obtained via a communication interface of the CBI device; and operate the CBI device, using the recalibrated neurostimulation signal parameters, to communicate information to the individual via neurostimulation of the one or more afferent sensory nerve fibers.

17. The CBI device of claim 16, wherein the CBI device is further configured to:

generate, based on the determined set of recalibrated signal parameters, a communication neurostimulation signal, configured to elicit an artificial sensation in a sensory cortex area via stimulating the one or more afferent sensory nerve fiber terminating in the specific sensory cortex area, wherein the artificial sensation is associated with a block of information to be communicated by the CBI device.

18. The CBI device of claim 16, wherein the set of reference bioelectric responses is associated with a set of artificial sensations that can be elicited by the CBI device via the neurostimulation interface in a sensory cortex area of the individual and that are associated with one or more blocks of information that can be communicated via the CBI device to the individual.

19. The CBI device of claim 16, wherein determining the set of reference bioelectric responses is performed based on one or more of:
    an initial or on-line calibration procedure involving the individual providing subjective feedback on artificial sensations elicited by a set of reference neurostimulation test signals;
    a plurality of reference calibration measurements performed on a plurality of individuals prior to determining the set of reference bioelectric responses for the individual; and
    an initial or online calibration procedure involving the individual performing one or more tasks with objectifiable outcomes that are supported by the operation of the CBI device and recording stimulation parameters and corresponding bioelectric responses that optimize performance of the task without recording subjective feedback by the individual.

20. The CBI device of claim 16,
    wherein a plurality of different neurostimulation test signals is generated and applied to the afferent sensory nerve fibers interleaved with a plurality of sensing periods of corresponding bioelectric responses of the afferent sensory nerve fibers.